(12) United States Patent
Mollenauer

(10) Patent No.: US 6,454,784 B1
(45) Date of Patent: *Sep. 24, 2002

(54) MINIMALLY INVASIVE METHOD OF HARVESTING EPIGASTRIC ARTERIES

(75) Inventor: Kenneth H. Mollenauer, Portola Valley, CA (US)

(73) Assignee: Thomas J. Fogarty, Portola Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,487

(22) Filed: Apr. 18, 2000

Related U.S. Application Data

(63) Continuation of application No. 09/083,911, filed on May 22, 1998, now Pat. No. 6,051,013.
(51) Int. Cl.[7] .............................................. A61B 17/00
(52) U.S. Cl. ........................................................ 606/192
(58) Field of Search .................................. 606/190, 191, 606/192, 194, 195, 198, 167, 157, 158, 159, 184

(56) References Cited

U.S. PATENT DOCUMENTS

| | | | | |
|---|---|---|---|---|
| 5,540,711 A | * | 7/1996 | Kieturakis | 606/192 |
| 5,591,183 A | * | 1/1997 | Chin | 606/159 |
| 5,601,581 A | * | 2/1997 | Fogarty et al. | 606/159 |
| 5,601,589 A | * | 2/1997 | Fogarty et al. | 606/192 |
| 5,653,726 A | * | 8/1997 | Kieturakis | 606/190 |
| 5,797,946 A | * | 8/1998 | Chin | 606/190 |
| 5,873,889 A | * | 2/1999 | Chin | 606/190 |

* cited by examiner

Primary Examiner—Michael J. Milano
Assistant Examiner—Vy Q. Bui
(74) Attorney, Agent, or Firm—K. David Crockett, Esq.; Crockett & Crockett

(57) ABSTRACT

A laparoscopic technique for harvesting the inferior epigastric artery and removing it from the body. The harvested inferior epigastric artery may be used as a bypass graft in a coronary or peripheral bypass operation.

1 Claim, 3 Drawing Sheets

MINIMALLY INVASIVE METHOD OF HARVESTING EPIGASTRIC ARTERIES

This application is a continuation of U.S. application Ser. No. 09/083,911 filed May 22, 1998, now U.S. Pat. No. 6,051,013.

FIELD OF THE INVENTION

This invention relates to minimally invasive surgery and blood vessel harvesting.

BACKGROUND OF THE INVENTION

Coronary bypass surgery is a well-known treatment for patients suffering from severe coronary artery disease. Bypass surgery involves implantation of a length of tubing, referred to as a graft, around a clogged segment of a coronary artery. The tube may be a synthetic material, a length of vein or artery from a donor, or a length of vein or artery harvested from the person undergoing the bypass operation. It is greatly preferred to use a length of vein or artery from the person undergoing the bypass operation, and the graft harvested from the patient is referred to as an autologous graft. Several blood vessels are commonly harvested for use as autologous grafts, including the saphenous vein, the internal mammary artery, and the inferior epigastric artery. Among the several blood vessels used for bypass grafts, the saphenous vein has been commonly used due to its ease of harvesting. The saphenous vein's superficial location along the inside of the leg (the saphenous vein can be easily felt under the skin, between the groin and the knee) makes it easy to locate and remove from the leg. The saphenous vein is well suited for use as a graft because it is about the same size (or a bit larger) as the coronary arteries. The saphenous vein is also somewhat redundant, and other veins in the leg readily take up the venous blood flow that normally flows through the saphenous vein, so that its removal from the leg does not seriously hamper blood supply in the leg. Some of the drawbacks to use of the saphenous vein are 1) unavailability (e.g. from prior vein stripping), 2) suboptimal long term patency rates and 3) its harvesting usually requires a sizable open wound along the entire length of the leg. We have previously suggested a minimally invasive method for harvesting the saphenous vein to avoid the large wound in our issued patent, Methods And Devices For Blood Vessel Harvesting, U.S. Pat. No. 5,601,581 (Feb. 11, 1997).

The internal mammary artery and inferior epigastric artery are suitable for use a coronary artery bypass grafts for several reasons. Because they are arteries and not veins, they are anatomically better suited to withstand the pressure of the arterial vasculature since they are arteries in the first place. They are about the same diameter as the coronary arteries. They tend to last longer without stenosis, clotting, aneurysm or other failures which require yet another intervention. For left-side cardiac bypass, the internal mammary artery is a preferable graft to the saphenous vein because it has been shown to stay open and unclogged longer. The inferior epigastric artery also performs well as a bypass graft, providing long term patency similar to that of the internal mammary artery.

The method described below is primarily concerned with harvesting the inferior epigastric artery. The location of the inferior epigastric arteries within the body makes them more difficult than the saphenous vein to harvest via the traditional open surgical approach. This traditional method entails increased operating time, and results in more invasive surgery. The inferior epigastric artery is located adjacent to and within the rectus abdominus muscle. It extends upwardly from the external iliac artery (just above the inguinal ligament, near the crease of the thigh), extends upwardly under the rectus muscle, and enters the rectus muscle. In many cases, it courses for some length through the rectus muscle. To harvest the inferior epigastric artery in the traditional method, the surgeon must make a long incision from the ribs to the lower abdomen. The skin, pre-peritoneal fat and rectus sheath must be incised, separated and retracted to provide access to the artery. The artery is removed from the body by ligating and dividing the side branches, then ligating the inferior epigastric artery both at its origin near the iliac artery and near its distal end in the upper abdomen, and dividing and removing the artery. This technique is illustrated in detail in Mills, et al., Techniques For Use Of The Inferior Epigastric Artery As A Coronary Bypass Graft, 51 Ann. Thoracic Surg. 208 (1991).

The inferior epigastric artery harvested according the method disclosed below may be used as a graft in coronary bypass surgery in place of the saphenous vein. It may also be used in other bypass operations such as the femoral-popliteal bypass in the leg. The harvested artery may also be used to provide a graft for muscle transfers performed by plastic surgeons to rebuild damaged parts of the body. Thus the method of harvesting the inferior epigastric artery may be used to reduce the trauma of the harvesting operation for a number of graft applications.

SUMMARY

The applicants have discovered a laparoscopic technique for harvesting the inferior epigastric artery and removing it from the body. The harvested inferior epigastric artery may be used as a bypass graft in a coronary bypass operation. The method avoids the open surgery and the large incision previously required for harvest of the inferior epigastric artery. This is advantageous because the artery is usually harvested for immediate use in the patient's own bypass operation. The method is also very quick and much less traumatic than the current open surgical method of harvest.

DETAILED DESCRIPTION OF THE INVENTION

Figure 1:
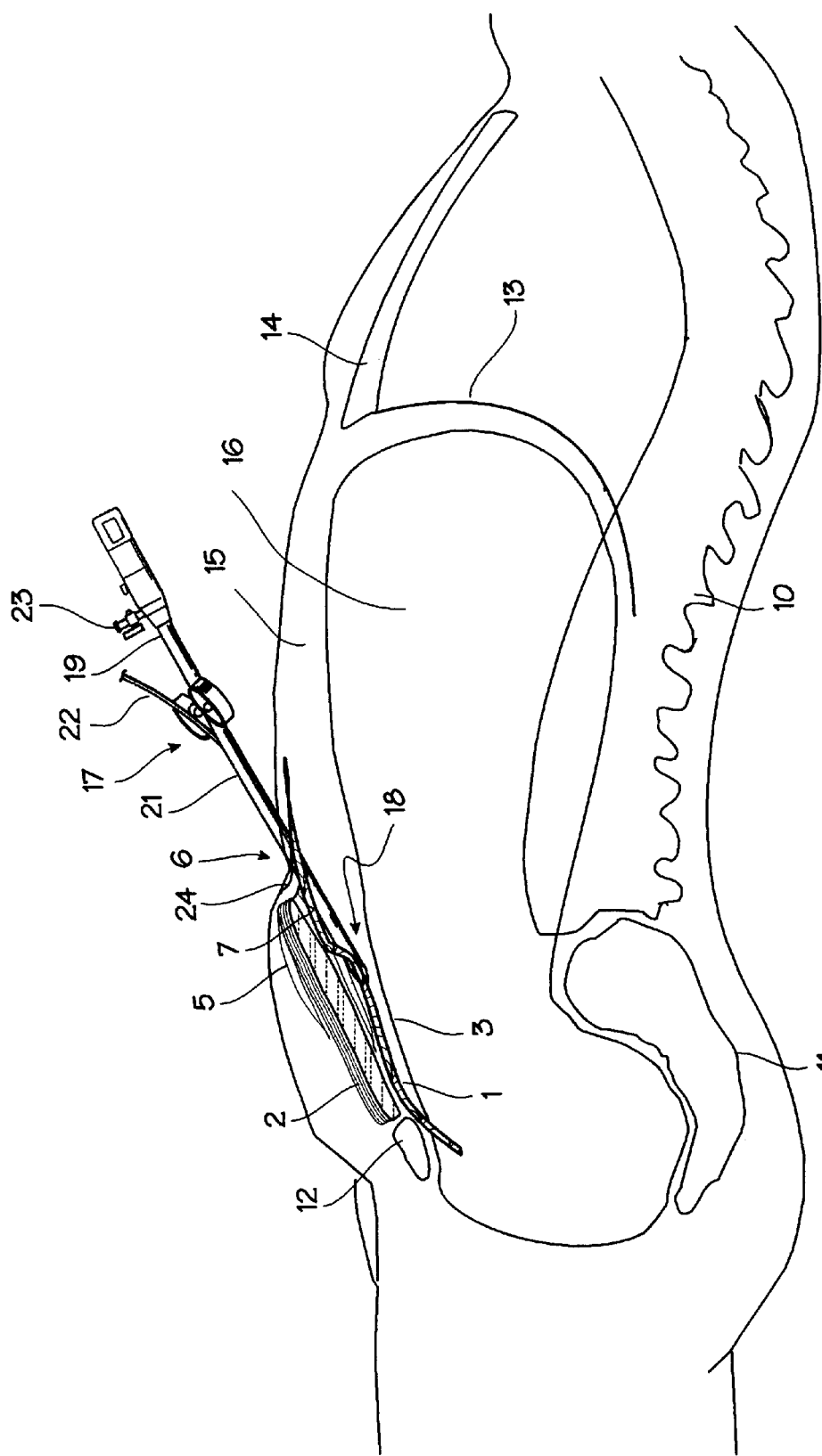
FIG. 1 is a cross section of the human body showing the location of the inferior epigastric artery and the method of exposing the inferior epigastric artery within a laparoscopic workspace.

FIG. 1 is a cross section of the human abdomen showing the location of the inferior epigastric artery in relation to the abdominal muscles, rectus sheath and peritoneum. FIG. 1 also serves to illustrate the method of accessing and harvesting this artery. The anatomy necessary to understanding the method is shown in FIG. 1. The inferior epigastric artery 1 is located in the lower abdomen, behind (posterior to) the rectus abdominus muscles 2 and in front of (anterior to) the peritoneum 3. The anterior rectus sheath 5 covers the lower part of the rectus abdominal muscles, and serves to join all the abdominal muscles (the obliques and the rectus abdominus muscles). It also borders with the umbilicus (belly button) 6. The posterior rectus sheath 7 covers the back side of the rectus abdominus muscles. The peritoneum is a sac which contains important abdominal organs such as the stomach and intestines. The inferior epigastric artery originates from the iliac artery 8 (see FIG. 2), and runs upwardly, under the rectus abdominus (its path is medial, off the center line of the body, and there is one inferior epigastric artery on each side of the body). The inferior epigastric artery ascends between the abdominal wall and the peritoneum for several inches until it connects with (anastomoses) the superior epigastric artery 9 (which is a branch of the internal mammary artery)(see FIG. 3). The anatomy of the inferior epigastric artery varies from person to person, but in most people it runs for some distance between the abdominal wall and the peritoneum. The inferior epigastric artery typically enters the rectus abdominus muscle below the umbilicus. (In some people, the inferior epigastric artery runs for substantially all of its length through the rectus muscle, which makes it very difficult to harvest.) Other anatomic structures are included in FIG. 1 as landmarks, including the spine 10, the sacrum 11, the symphysis pubis 12, the diaphragm 13, the sternum 14, the abdominal wall 15 and the peritoneal cavity 16.

The inferior epigastric artery 1 can be harvested without a large abdominal wall incision, and without cutting open the abdomen or retracting the rectus abdominus as described above in the background section. The method of exposing the inferior epigastric artery is similar to the method of exposing a hernia according to Kieturakis, et al, Apparatus and Method for Developing an Anatomic Space for Laparascopic Procedures with Laparascopic Visualization, U.S. Pat. No. 5,540,711 (Jul. 30, 1996). With the aid of a dissecting balloon device 17, the rectus abdominus muscle (s) and the rectus sheath can be dissected away from the peritoneum, and an extra-peritoneal space 18 may be created to provide for visualization of this area. According to Kieturakis, the creation of this space is used for repair of an inguinal hernia, which is a condition in which the peritoneal contents inadvertently protrude through the inguinal ring near the symphysis pubis 12. The balloon dissection device can include an introducer portion 19, a balloon 20 (not visible in this view) under a tear away sheath 21, a balloon inflation tube 22 and an insufflation port 23.

The balloon dissecting device is inserted near the belly button (umbilicus) 6. The insertion is made through an infra-umbilical incision 24 followed by a small incision in the rectus sheath very close to the belly button. The balloon dissecting device is then pushed into the incision, through the small incision in the rectus sheath, and pushed and advanced inferiorly between the anterior surface of the peritoneum 3 and the posterior surface of the rectus abdominus muscle 2, thus entering the extra-peritoneal area 18 where the inferior epigastric arteries usually are found. The balloon dissecting device serves as a tunneling device, and its progress is followed by the surgeon by watching and feeling the progress of the device under the skin of the lower abdomen. The advance of the device is continued until it approaches the symphysis pubis 12.

Figure 2:
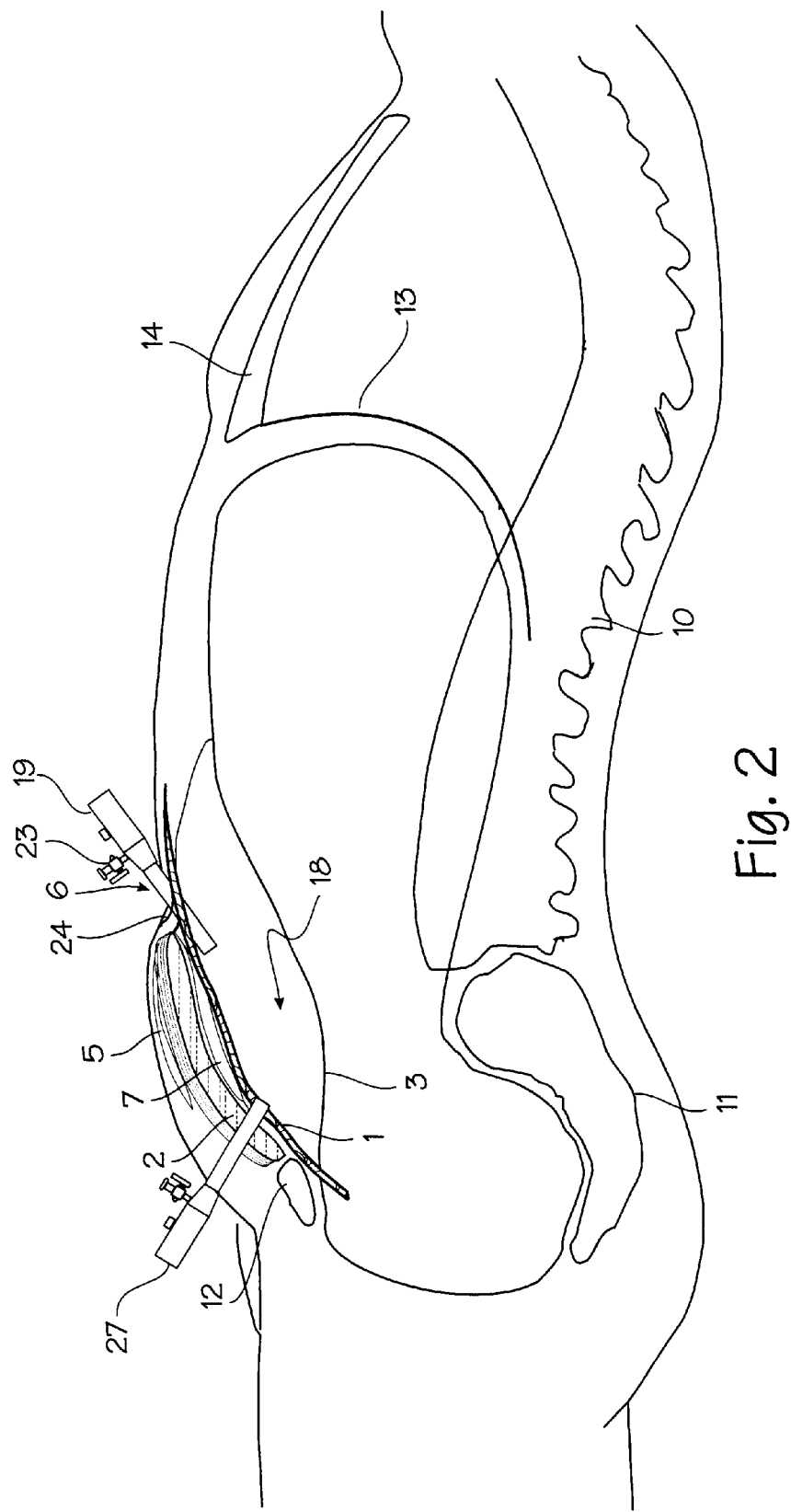
FIG. 2 is a cross section of the human body showing the location of the inferior epigastric artery and the method of exposing the inferior epigastric artery within a laparoscopic workspace.

After the balloon dissection device 17 is properly positioned, with the tip extending approximately to the symphysis pubis, the sheath 21 of the device is withdrawn and the balloon inflated. As the balloon is inflated, it lifts and dissects the abdominal wall (the rectus sheath and rectus abdominus muscles) away from the peritoneum. The balloon dissecting device is then deflated and withdrawn. The introducer portion 19 of the balloon dissecting device is left in place, and a gas such as carbon dioxide is injected into the extra-peritoneal space. This process, known as insufflation, serves to inflate the extra-peritoneal space like a balloon, keeping the rectus abdominus muscle 2 high above the peritoneum 3 to provide a work space with plenty of room for laparoscopic instruments and for visualization through an endoscope. FIG. 2 illustrates the condition of the body during insufflation, and shows that the work space 18 is enlarged during insufflation. The skin and abdominal wall (abdominal muscles and/or rectus sheath) may then be pierced with additional laparoscopic access ports 27 and 29 to provide alternative sites for insufflation or laparoscopic access to the space.

A laparoscope may be inserted into the space through the introducer 19 to view the space and find the inferior epigastric artery. The inferior epigastric arteries of the typical patient are clearly visible, running along the posterior rectus sheath.

Figure 3:
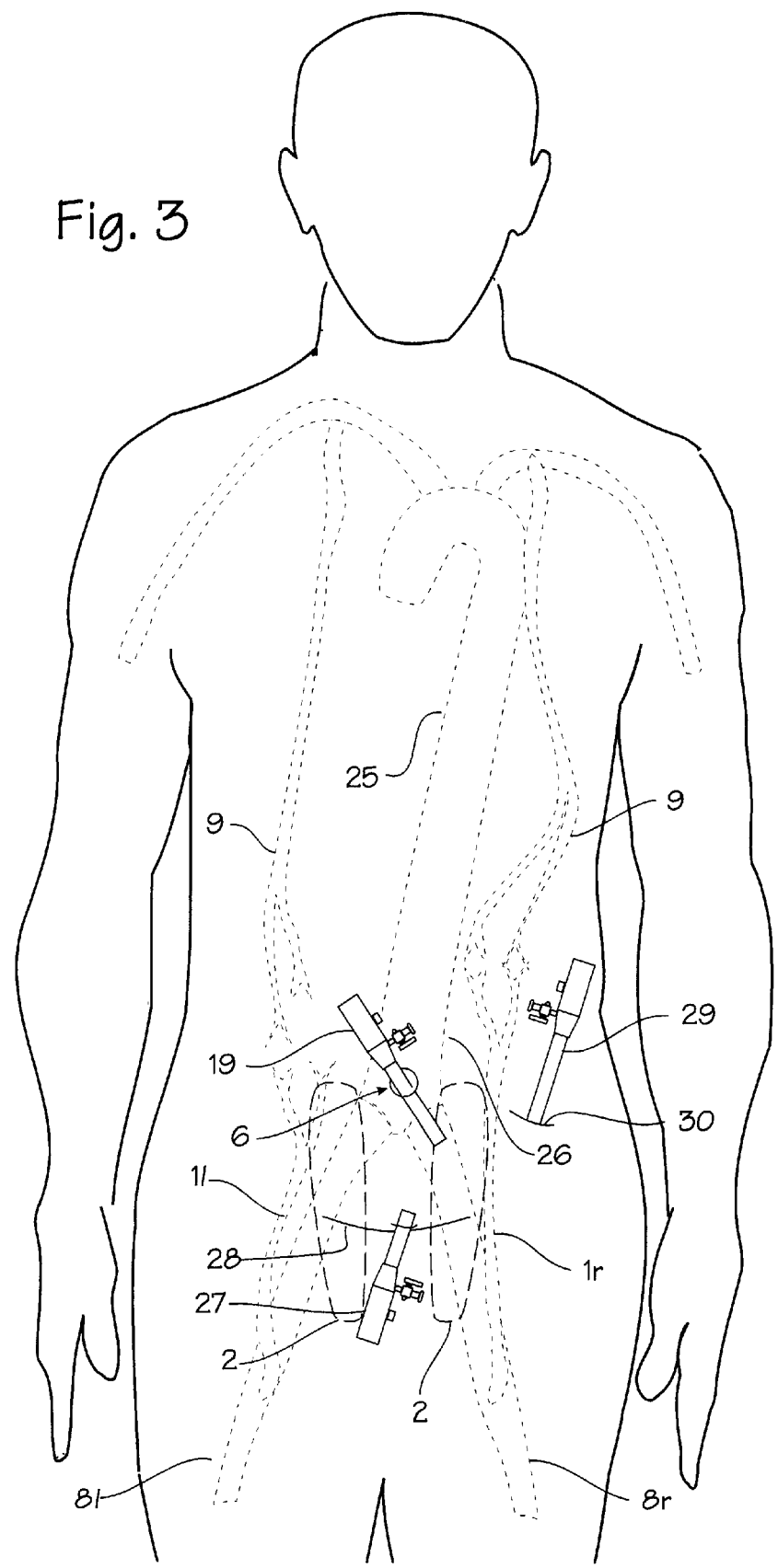
FIG. 3 is an anterior view of the human body showing preferred placement of laparoscopic access ports for harvesting the inferior epigastric artery.

FIG. 3 shows an anterior view of the human torso and illustrates the harvesting method. The inferior epigastric arteries 1l and 1r are shown rising from the external iliac arteries 8l and 8r, respectively. The inferior epigastric arteries 1l and 1r are under the rectus abdominus muscles 2. Note that the inferior epigastric artery 1r extends for some distance above the umbilicus 6, which is common, while the inferior epigastric artery 1l reaches to about the umbilicus 6, which is also common. The first laparoscopic port 19 is inserted near the umbilicus 6. FIG. 3 also shows the aorta 25, 26 to illustrate the relative position of the inferior epigastric artery within the body. As shown in FIG. 3, additional laparoscopic access ports are installed, and their placement may be a matter of personal preference for the surgeon. Preferably, a second access port 27 is installed through a small incision near the arcuate line 28 near the midline of the body. A third access port 29 may be installed lateral to the rectus sheath, at incision 30. Laparoscopic tools are inserted through any of the access ports. Any connective tissue covering the artery is separated away from the inferior epigastric artery, and its branches are located, ligated by sutures or clips, and divided by cutting with laparoscopic scissors. The inferior epigastric artery itself is then ligated near its origin near the iliac artery, and is also ligated high along the abdominal wall at a convenient location.

In cadaver studies, the inferior epigastric artery has been successfully harvested according to this method. Approximately 5.5 inches (about 13 cm) of the inferior epigastric artery was found below the point at which it entered the posterior rectus abdominus sheath was harvested in approximately five to ten minutes. The cadaver study was done with the three port method described above. With laparoscopic graspers and cutters, the harvested portion of the inferior epigastric artery was easily separated from its branch vessels and was easily divided from the proximal portion and distal portion of the artery which were left in place. While common laparoscopic tools were used in the cadaver study, special blood vessel harvesting tools may be used. For example, our prior patent, Methods And Devices For Blood Vessel Harvesting, U.S. Pat. No. 5,601,581 (Feb. 11, 1997) discloses a hooked blood vessel harvesting tool which may be readily employed in harvest of the inferior epigastric artery. Also, while the access port placement and insufflation described above have been used to describe the invention, alternative access points and methods of creating the laparoscopic work space, or gaining access to the dissectable plane between the rectus muscle and the peritoneum with minimal invasion into the abdomen, may be employed to successfully expose and harvest the inferior epigastric artery.

In many cases it will suffice to harvest the portion of the inferior epigastric artery that resides between the peritoneum and the rectus abdominus muscle, and leave the portion of the inferior epigastric artery that runs within the rectus abdominus muscle in the body. If desired, this portion of the inferior epigastric artery may be harvested by carefully ligating and dividing the many side branches of the inferior epigastric artery. Working space along the inferior epigastric artery, within the rectus abdominus muscle, can be created using a balloon dissecting device such as that shown in our earlier patent, Methods and Devices for Blood Vessel Harvesting, U.S. Pat. No. 5,601,589 (Feb. 11, 1997). With a balloon inserted along the inferior epigastric artery within the rectus abdominus muscle, the rectus abdominus muscle can be gently separated or dissected away from the inferior epigastric artery, leaving a small endoscopic space for the insertion of tools necessary to ligate and divide the side branches of the inferior epigastric artery.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method of harvesting the inferior epigastric artery of a human patient comprising the steps of:

inserting an uninflated dissecting balloon between the rectus abdominus muscles and the peritoneum of the patient;

inflating the balloon to create an expanded extra-peritoneal space between the rectus abdominus muscles and the peritoneum of the patient;

removing the balloon from the extra-peritoneal space;

maintaining the expanded extra-peritoneal space in the expanded condition;

inserting at least one laparoscopic tool into the expanded extra-peritoneal space;

cutting the inferior epigastric artery from the body with laparoscopic tool; and removing the inferior epigastric artery from the extra-peritoneal space.

* * * * *